United States Patent
Hirzmann et al.

(10) Patent No.: US 10,292,659 B2
(45) Date of Patent: May 21, 2019

(54) VEHICLE OPERATING ELEMENT AND METHOD FOR NONINVASIVELY MEASURING BIOMOLECULES

(71) Applicant: TRW Automotive GmbH, Alfdorf (DE)

(72) Inventors: Guido Hirzmann, Sailauf (DE); Martin Seyffert, Pfullingen (DE); Raymond Glocker, Aschaffenburg (DE); Chunnan Chen, Aschaffenburg (DE); Hendrik Dietrich, Aschaffenburg (DE)

(73) Assignee: TRW AUTOMOTIVE GMBH, Alfdorf (DE)

(*) Notice: Subject to any disclaimer, the term of this patent is extended or adjusted under 35 U.S.C. 154(b) by 16 days.

(21) Appl. No.: 15/514,853

(22) PCT Filed: Sep. 22, 2015

(86) PCT No.: PCT/EP2015/001878
§ 371 (c)(1),
(2) Date: Mar. 28, 2017

(87) PCT Pub. No.: WO2016/050340
PCT Pub. Date: Apr. 7, 2016

(65) Prior Publication Data
US 2018/0228440 A1    Aug. 16, 2018

(30) Foreign Application Priority Data
Sep. 29, 2014   (DE) .................. 10 2014 014 071

(51) Int. Cl.
*H01Q 1/32* (2006.01)
*H01Q 1/38* (2006.01)
(Continued)

(52) U.S. Cl.
CPC .......... *A61B 5/6893* (2013.01); *A61B 5/0537* (2013.01); *A61B 5/1477* (2013.01);
(Continued)

(58) Field of Classification Search
CPC ............ G01N 27/026; G01N 33/4972; G01N 27/4074; A61B 5/1477; A61B 5/4845;
(Continued)

(56) References Cited

U.S. PATENT DOCUMENTS

| | | | | |
|---|---|---|---|---|
| 5,944,661 A | * | 8/1999 | Swette | ............... A61B 10/0064 |
| | | | | 204/403.06 |
| 2003/0120139 A1 | * | 6/2003 | Duval | ...................... A61B 5/18 |
| | | | | 600/363 |

(Continued)

*Primary Examiner* — Mirza F Alam
(74) *Attorney, Agent, or Firm* — Tarrolli, Sundheim, Covell & Tummino LLP (57) ABSTRACT

The invention relates to a vehicle operating element (12) comprising a sensor (14) for non-invasive measurement of biomolecules in the blood of an operator of a vehicle operating element (12) by means of electrochemical impedance spectroscopy, comprising at least one antenna (16) which includes at least a first conductive layer, a second conductive layer and an insulating layer being sandwiched between the two conductive layers. By means of the second conductive layer an excitation signal can be coupled out and an off-resonance excitation signal can be coupled into the antenna (16). Furthermore, a method of non-invasive measurement of biomolecules and a method of operating a vehicle are described.

30 Claims, 4 Drawing Sheets

(51) Int. Cl.
*A61B 5/00* (2006.01)
*A61B 5/053* (2006.01)
*A61B 5/145* (2006.01)
*A61B 5/1477* (2006.01)
*B60K 28/02* (2006.01)
*G01N 27/02* (2006.01)
*H01Q 9/28* (2006.01)

(52) U.S. Cl.
CPC ........ *A61B 5/14546* (2013.01); *A61B 5/4845* (2013.01); *A61B 5/6898* (2013.01); *B60K 28/02* (2013.01); *G01N 27/026* (2013.01); *H01Q 1/3291* (2013.01); *H01Q 1/38* (2013.01); *H01Q 9/285* (2013.01); *A61B 2503/22* (2013.01); *A61B 2562/02* (2013.01)

(58) Field of Classification Search
CPC .............. A61B 5/14546; A61B 5/0537; A61B 10/0035; A61B 2010/0009; A61B 5/18
See application file for complete search history.

(56) References Cited

U.S. PATENT DOCUMENTS

| | | | |
|---|---|---|---|
| 2008/0146892 A1* | 6/2008 | LeBoeuf | G16H 50/30 600/300 |
| 2008/0185295 A1* | 8/2008 | Briman | G01N 33/5438 205/777.5 |
| 2010/0057368 A1* | 3/2010 | Afeyan | A61K 49/0004 702/19 |
| 2010/0269566 A1* | 10/2010 | Carroll | A61B 5/14546 73/23.3 |
| 2013/0070043 A1* | 3/2013 | Geva | B60K 28/066 348/14.02 |
| 2015/0015276 A1* | 1/2015 | Glocker | G01R 1/067 324/649 |

\* cited by examiner

Fig. 7

VEHICLE OPERATING ELEMENT AND METHOD FOR NONINVASIVELY MEASURING BIOMOLECULES

RELATED APPLICATIONS

This application corresponds to PCT/EP2015/001878, filed Sep. 22, 2015, which claims the benefit of German Application No. 10 2014 014 071.7, filed Sep. 29, 2014, the subject matter of which are incorporated herein by reference in its entirety.

BACKGROUND OF THE INVENTION

The invention relates to a vehicle operating element as well as a method of non-invasive measurement of biomolecules, especially of lactate, alcohol and/or urea.

It is known from the state of the art that vehicles include a plurality of sensors increasing the safety during operation of the vehicle. For example, sensors for monitoring the driving behavior of the operator are provided so as to conclude a health condition and, resp., a condition of fitness to drive of the operator therefrom. Sensors of this type may evaluate, for example, the steering behavior of the operator or may follow the movement of his/her eyes so as to determine the operators fatigue.

It has turned out to be a drawback of said sensors that they can determine the operator's condition only on the basis of the measurement of indirect parameters such as motion sequences or posture. Therefore, sensors of this type can only detect conditions that have already occurred. Directly imminent changes of condition which will affect the operator's driving behavior and health cannot be detected by said sensors, however.

SUMMARY OF THE INVENTION

It is the object of the invention to provide a vehicle operating element which is capable of detecting upcoming changes of the health condition and, resp., the condition of fitness to drive of the operator.

According to the invention, the object is achieved by a vehicle operating element comprising at least one sensor for non-invasive measurement of biomolecules in the blood of an operator of a vehicle operating element by means of electrochemical impedance spectroscopy, comprising at least one antenna including at least a first conductive layer, a second conductive layer and an insulating layer being sandwiched between the two conductive layers, and wherein by means of the first conductive layer and/or the second conductive layer an excitation signal can be coupled out as well as an off-resonance excitation signal can be coupled into the antenna.

It is the basic idea of the invention to provide a vehicle operating element with a sensor which directly detects the blood values of the operator so as to obtain information about the current health condition and/or the condition of fitness to drive as well as about imminent changes thereof. Typically, blood examinations in the medical field are only carried out by invasive measurements, which is not possible in the automotive field, however. The sensor of the operating element of the invention includes an antenna which, due to its structure, can couple out electromagnetic radiation of a defined frequency that becomes free progressive waves. The excited free progressive waves propagate through the skin into the operators blood stream and in the latter excite at least one type of biomolecules to oscillate, if the defined frequency of the resonance frequency corresponds to this type of biomolecules.

Based on the vibration excitations of the biomolecules through the antenna, the coupled-out electromagnetic excitation signal becomes off-resonance. Accordingly, the phase of the off-resonance excitation signal is shifted and the amplitude of the off-resonance excitation signal is equally varied. The off-resonance excitation signal can be detected by the antenna. By means of impedance spectroscopy examining the change of the wave function of particular frequencies, especially the phase thereof and the amplitude thereof, between the coupled-out excitation signal and the off-resonance excitation signal, the presence and the concentration of the biomolecules having known resonance frequencies can be detected in the operator's blood.

Since in the case of measurement of the blood values and, resp., of the biomolecules merely electromagnetic waves are radiated via the antenna and off-resonance electromagnetic waves are received, the measurement may be carried out in a noninvasive manner so that the measurement of the biomolecules is a non-invasive electrochemical impedance spectroscopy.

The biomolecules to be measured may be lactates, alcohol and/or urea each of which has a different resonance frequency. It is known, for example, that the lactate values are changing in the case of imminent heart attack so that an imminent heart attack can be detected in sufficient time by means of the non-invasive measurement of the lactate value of the operator. Typically, a detectable change of the lactate values can be detected already ten minutes before a heart attack will occur. Moreover, it is insignificant whether the electromagnetic waves couple into arterial or venous blood, as the biomolecules can be detected in both blood circulations.

One aspect of the invention provides that the first or second conductive layer is formed to have an edge-side structure, especially a polygonal edge. By means of the edge-side structuring of the conductive layer comb structures may be formed so that the antenna exhibits better coverage of frequencies. Due to the fractal structures and, resp., the comb structures a broader frequency band can be received by the antenna by reason of the accompanying Sierpinski effect. For example, lactate has a resonance frequency at approx. 170 MHz (longitudinal oscillation) and, resp., at 390 MHz (transversal oscillation), whereas ethanol has a resonance frequency at approx. 600 MHz. This broad frequency spectrum may be covered by the antenna by virtue of the edge-side structuring. It is possible in general to cover a frequency spectrum of from 30 MHz to 900 MHz by the antenna.

In accordance with an embodiment of the invention, the first conductive layer and the second conductive layer are arranged substantially in parallel to each other. Depending on the orientation and arrangement of the conductive layers, different free progressive waves which may be preferred depending on the arrangement of the antennas at the vehicle operating element can be generated by the excitation signal.

In an alternative embodiment, the second conductive layer is substantially curved and extends, especially eccentrically, around the first conductive layer.

Another embodiment of the invention provides a third conductive layer which is electrically coupled to the first or second conductive layer and forms a connecting layer, especially wherein the conductive layers of the connecting layer are spaced from each other so that the second or, resp., the first conductive layer is arranged between the conductive layers of the connecting layer. In this way, the efficiency of the antenna may be improved with the construction height remaining constant or being slightly increased, as the connecting layer and the interposed layer form two dipoles so that an efficient and at the same time sensitive antenna is provided.

According to another aspect of the invention, the at least one antenna is designed to be flexible. This is achieved by the fact that the electrically conductive layers are thin layers so that they are flexible. For example, a conductive layer has a thickness of less than 50 µm, especially between 10 µm and 35 µm. The interposed insulating layer, too, has a thickness within the same magnitude. Hence the at least one antenna may have a thickness of from 30 µm to 300 µm, thus allowing arrangement of the same in a curved manner on a steering wheel rim, for example.

Furthermore, there may be provided a cover layer to be contacted by the operator which forms the outermost layer of the antenna and is especially made from an electrically insulating material. The cover layer may be a film, diaphragm, leather skin, wooden layer ceramic, glass or varnish, which is dependent on how the respective vehicle operating element is configured. The cover layer on the one hand acts as a contact shield of the sensitive antenna structure and, on the other hand, as an optical element so that the sensor is optically adapted to the vehicle operating element. The sensor may be provided to be almost invisible within the vehicle operating element.

Another aspect of the invention provides the antenna to be configured as a dipole antenna or a multi-pole antenna. In this way, the efficiency of the antenna may be further increased.

Further, the at least one antenna may comprise a dielectric insert, especially made from fine ceramics, for improving the sensitivity of the antenna in the low frequency range. The dielectric insert helps to achieve a higher dielectric constant so that small antenna structures are sensitive to large wavelengths. The optional dielectric insert thus increases the frequency coverage of the antenna. In this way, for example, the improved frequency coverage can be assisted by virtue of the structured borders.

In accordance with another aspect of the invention, a control and evaluating unit for controlling the at least one antenna as well as for evaluating the off-resonance excitation signals received by the at least one antenna is provided. Via the control and evaluating unit the wave to be coupled out is excited, as the excitation frequency is predetermined. At the same time, the off-resonance excitation signal received by the antenna may be analyzed. By way of the off-resonance excitation signal the presence of a respective biomolecule can be detected in the operator's blood.

In particular, the control and evaluating unit is formed so that it generates different excitation frequencies for the antenna. This ensures that via the at least one antenna electromagnetic waves having different frequencies can be generated which excite the different biomolecules to be detected with their excitation frequencies different from each other, if said biomolecules are present in the operator's blood.

Furthermore, the control and evaluating unit may be configured so that it evaluates wave functions of off-resonance excitation signals and, based on the off-resonance, establishes the presence of biomolecules. The control and evaluating unit thus can carry out the mathematic calculations of an impedance spectroscopy.

Another aspect of the invention provides that the vehicle operating element is part of a vehicle steering wheel, actuating lever or shift lever of the vehicle. This ensures that the operator of the vehicle necessarily contacts the respective vehicle operating element during operation of the vehicle so that the biomolecules in the operator's blood are measured non-invasive during operation of the vehicle.

Moreover, plural antennas may be arranged to be spread over the vehicle operating element. This increases the probability that during operation the operator is located within the range of the detection field of at least one of the antennas so that measurement is possible via the respective antenna.

The plural antennas may be associated with one single measuring point so that a higher resolution per measuring point is resulting. This is especially advantageous when the operator's hand does not completely rest on the measuring point. Furthermore, the measuring results of the plural antennas per measuring point can be compared to each other and verified. The antennas are especially arranged in groups on the respective measuring point.

In general, the areas detected by the antennas may be referred to as measuring cells, wherein one measuring point may comprise one measuring cell or plural measuring cells. Accordingly, spread over the vehicle operating element plural measuring points may be provided, each comprising one antenna or plural antennas.

In accordance with another embodiment of the invention, a heating layer which is especially adjacent to or integrated in an insulating layer may be provided. Thus, the antenna can simultaneously actively heat the vehicle operating element, which increases the comfort for the operator.

Alternatively or in addition, a measuring instrument may be provided which is formed for non-invasive measurement of biomolecules, especially lactate, alcohol and/or urea, in the blood of an operator of a vehicle by means of electrochemical impedance spectroscopy, the measuring instrument being adapted to be coupled to a control and evaluating unit of the vehicle. The measuring instrument may be, for example, a wristband or any other accessory worn by the operator. Said wristband may be configured separately or as part of another device, especially a so-called smartwatch. The wristband is in permanent contact with a part of the body of the operator, which enables high measuring accuracy, in particular as the measurements are always carried out at the same part of the body. The data detected by the measuring instrument can be evaluated in the measuring instrument itself or may be transmitted to the control and evaluating unit of the vehicle for evaluating the data. As an alternative, the data may also be transmitted to an external evaluating unit, for example a cell phone, especially a so-called smartphone.

The transmission of the data is preferably wireless so that the operator's freedom of movement is not restricted.

The measuring instrument includes at least one antenna which comprises at least a first conductive layer, a second conductive layer and an insulating layer being sandwiched between the two conductive layers, and wherein via the first conductive layer and/or the second conductive layer an excitation signal can be coupled out as well as an off-resonance excitation signal can be coupled into the antenna. The antenna of the measuring instrument is structured substantially analogously to the antenna in the vehicle operating element, with the same advantages resulting analogously.

The object of the invention is further achieved by a method of non-invasive measurement of biomolecules, especially lactate, alcohol and/or urea, in the blood of an operator of a vehicle by means of electrochemical impedance spectroscopy using a vehicle operating element of the afore-described type and/or a measuring instrument of the afore-described type. The vehicle operating element and/or the measuring instrument include(s) a sensor suited for non-invasive measurement of biomolecules. Hence the method enables to detect imminent changes of the health condition and, resp., the condition of fitness to drive in good time so that active intervention will be possible, the speed will be increasingly reduced, warning signals will be transmitted or the vehicle will not be started at all.

In particular, plural biomolecules having different excitation frequencies can be measured. In this way, the condition of the operator of the vehicle can be precisely determined, as plural biomolecules allowing information about different conditions of the operator can be measured simultaneously or successively.

One aspect of the invention provides that the biomolecules in the operators blood are measured contact-less. The part of the body to be measured should be within the near field of the antenna so that a sufficiently high power can be coupled in and the antenna can detect the off-resonance excitation signal in a sufficiently proper manner. However, no direct contact with the sensor or the antenna is necessary.

According to one aspect of the invention, the control and evaluating unit evaluates the complex impedance between the excitation signal and the off-resonance excitation signal for quantifying the concentration of the biomolecules in the operator's blood. The complex impedance the evaluation of which serves for calculating the concentration of the biomolecules can be concluded from the change of the amplitude and the phase between the excitation signal and the off-resonance excitation signal.

Moreover, based on the complex impedance the control and evaluating unit can determine the measuring surface and/or measuring points and/or number of operators underlying the measurement. The control and evaluating unit may find out on the basis of the evaluation of the complex impedance whether there is a contact at all and whether the operator is within the detection range of the sensor with a body part, as otherwise there will be no off-resonance of the excitation signal. It may further be determined on the basis of the evaluation which area of the operator of the vehicle is located within the range of the sensor, as the examined volume can be concluded from the real part of the complex impedance, wherefrom an average area can be concluded. Furthermore, a different operator can be concluded from strongly different results of the measurement.

Another aspect of the invention provides that the control and evaluating unit controls the at least one antenna in a synchronized manner, wherein, if plural antennas are provided, the control and evaluating unit sequentially controls the antennas. This may increase the efficiency of the sensor, as checking of the biomolecules is required at particular time intervals only. Sequential control is interesting especially when a previously existing contact with one of the antennas has been lost so that a new antenna is searched by which measurement is possible as the operator is located in the near field of such antenna.

Moreover, a memory may be provided in which the established values can be stored, with the control and evaluating unit calculating, especially extrapolating, trends on the basis of the stored values so as to establish forecasts about the value development. This enables a course of the concentration of the respective biomolecules to be stored and evaluated so as to predict an imminent change of the concentration of a respective biomolecule from which a change of the health condition and, resp., of the general condition of the vehicle operator can be concluded.

In addition, the object of the invention is achieved by a method of operating a vehicle, wherein a method of non-invasive measurement of biomolecules of the afore-mentioned type is carried out and wherein at least one vehicle system is operated depending on the result of the method of non-invasive measurement of biomolecules. At first the control and evaluating unit can be directly connected to a central control unit of the vehicle so that the information established by the control and evaluating unit are made available to all components of the vehicle. Accordingly, a visual or acoustic warning message, for example, may be displayed or notified to the vehicle operator, when a critical condition has been found due to the varying concentration of a biomolecule. Moreover, further vehicle safety systems can be controlled as a function of the detected values and, resp., the sensitivity thereof can be varied, e.g. a distance and/or speed control unit, so that they react more sensitively to changes, for example. In addition, the central control unit may activate vehicle safety systems which have been manually deactivated before, such as a lane-keeping system, a traffic jam assistant and/or a steering assistant, by reason of a detected critical condition or a predicted critical condition. In an extreme case, even the control and/or governing of all functions of the vehicle can be completely taken over by the central control unit and a brake action, especially emergency braking, can be initiated. In so doing, the central control unit may also make an emergency call.

If plural antennas which are associated with one measuring point are provided, the measuring results of said antennas can be compared to each other and verified. When the measuring point is not completely contacted, it is resulting herefrom that the measuring results of the antennas are different from each other. The control unit can find out which measuring results are to be traced back to a non-contacted area of the measuring point and can appropriately exclude them or leave them out of consideration.

BRIEF DESCRIPTION OF THE DRAWINGS

Further advantages and characteristics of the invention will be evident from the following description and the drawings which are referred to, wherein.

DESCRIPTION

Figure 1:
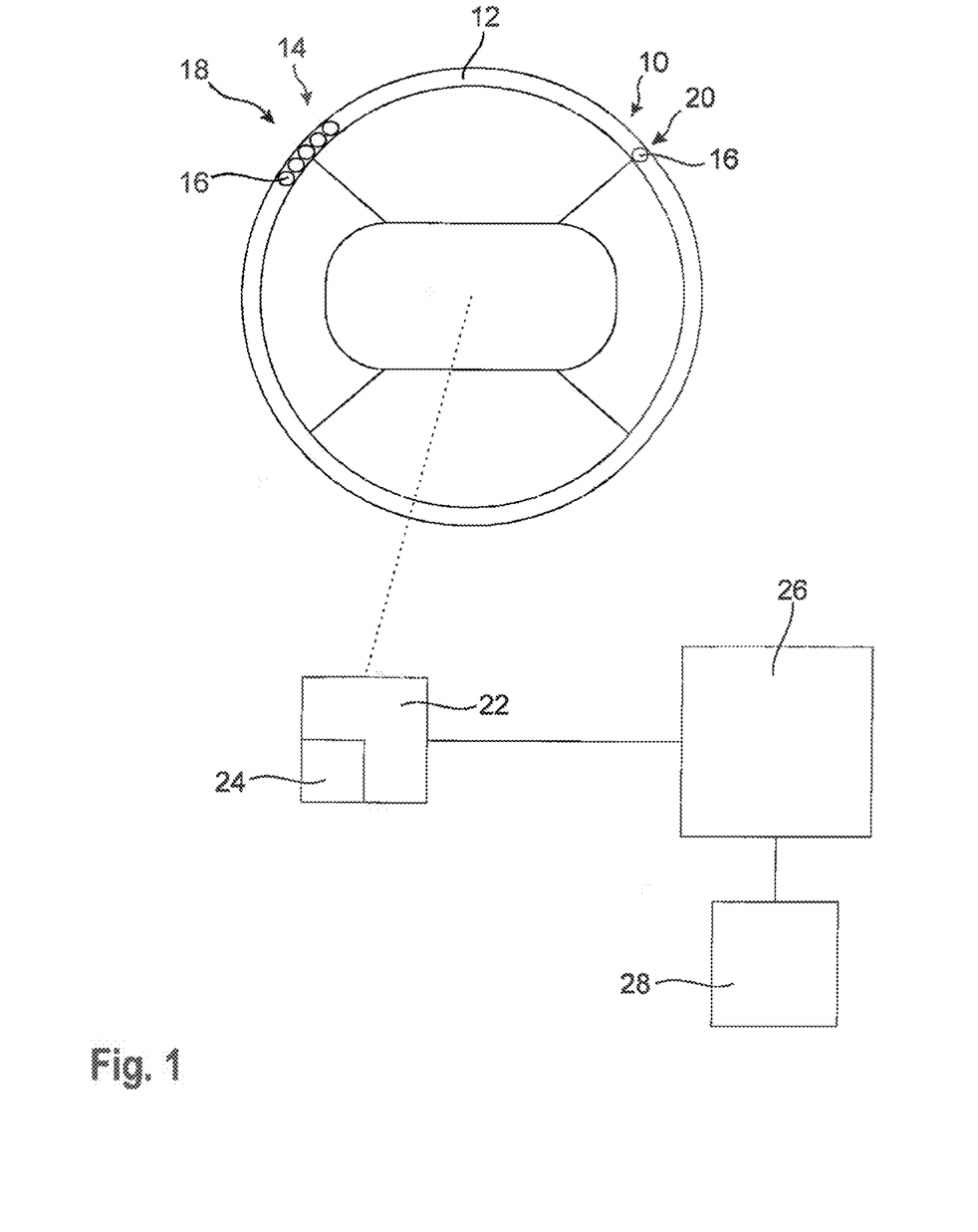
FIG. 1 shows a schematic representation of a vehicle operating element according to a first embodiment of the invention.

FIG. 1 shows a vehicle steering wheel 10 comprising a steering wheel rim which forms a vehicle operating element 12.

The vehicle operating element 12 includes a sensor 14 for non-invasive measurement of biomolecules in the blood of an operator of the vehicle operating element 12 and, resp., of the steering wheel 10. For this purpose, the sensor 14 includes plural antennas 16 the structure of which shall be illustrated below by way of FIGS. 2 to 4.

The antennas 16 are arranged to be spread over the vehicle operating element 12, wherein they are arranged in areas 18, 20 of the vehicle operating element 12 which the operator of the steering wheel 10 typically encompasses. In the shown embodiment, these are the typical positions of the steering wheel 10 which a driver's hands are intended to encompass, wherein this position is also known as "10 to 2". This ensures that the antennas 16 of the sensor 14 are associated with the palm or the fingers.

The first area 18 in the shown embodiment comprises five antennas 16, whereas the second area 20 includes merely one antenna 16. Alternatively, the antennas 16 may also be arranged to be spread over the entire steering wheel rim at regular intervals.

The antennas 16 arranged in groups in the first area 18 can be arranged such that they are associated with one single measuring point so that said one measuring point can be highly resolved, as will be described hereinafter.

The antennas 16 are generally configured so that they are adapted to excite biomolecules present in the operator's blood by means of electromagnetic radiation. This means that the antennas 16 can emit an excitation signal having a frequency which corresponds to the resonance frequency of the biomolecules to be measured.

For this purpose, the antennas 16 are coupled to a control and evaluating unit 22 which may be provided in the vehicle steering wheel 10 itself or at a different place. The control and evaluating unit 22 serves for controlling the antennas 16 so that the control and evaluating unit 22 controls the antennas 16 so that the latter generate the electromagnetic waves with different excitation frequencies.

The frequencies may especially be frequencies of the biomolecules to be typically examined such as lactate, methanol and/or urea, with lactate having an excitation frequency of 175 MHz+/−50 MHz, ethanol having an excitation frequency of 600 MHz+/−50 MHz and urea having an excitation frequency of 300 MHz+/−50 MHz.

In order to obtain different excitation frequencies it may also be provided that the control and evaluating unit 22 passes a complete frequency band, i.e. from e.g. 30 MHz to 900 MHz.

On the basis of the excitation of the biomolecules by the electromagnetic waves with the appropriate excitation frequencies and, resp., the excitation signals, the emitted excitation signal becomes off-resonance. The off-resonance excitation signal differs from the excitation signal to the effect that it is phase-shifted and has a different amplitude, especially an attenuated amplitude.

Moreover, the off-resonance excitation signal superimposes the excitation signal so that in the case of excitation of a biomolecule two different signals are located in the near field of the antenna 16.

The antennas 16 are generally configured so that they are equally adapted to detect the off-resonance excitation signal, thus causing the off-resonance excitation signal to be transmitted to the control and evaluating unit 22.

The transmission of the excitation signal from the control and evaluating unit 22 to the antennas 16 as well as the transmission of the off-resonance excitation signal from the antennas 16 to the control and evaluation unit 22 may be performed via coaxial lines by which the antennas 16 and the control and evaluating unit 22 are coupled to each other.

The control and evaluating unit 22 is further configured to evaluate the off-resonance excitation signals and to establish a concentration of the excited biomolecule on the basis of the excitation signal and the off-resonance excitation signal. For determining the concentration of the excited biomolecule the control and evaluating unit 22 evaluates the complex impedance between the excitation signal and the off-resonance excitation signal.

The real part of the complex impedance can be evaluated for determining the sample volume, whereas the imaginary part of the complex impedance is used for quantifying the biomolecules. Hence the concentration of the excited biomolecule in the blood of the operator can be determined by means of the ratio of the imaginary part and the real part of the complex impedance.

Moreover, the control and evaluating unit 22 can establish the underlying measuring surface, the measuring points and/or the number of operators on the basis of the evaluation of the complex impedance. This may be performed, on the one hand, by the control and evaluating unit 22 detecting how many of the plural antennas 16 are covered by the hand or any other body part of the operator so that the number of antennas 16 by which measurement is possible at all is determined.

If plural antennas 16 are associated with one measuring point, the control and evaluating unit 22 can exclude the measuring results of those antennas 16 which are not covered by an object to be measured, i.e. the operator's hand. This allows measuring a useful measuring result at a measuring point, although the measuring point is encompassed only partially by the operator. In this way, the measuring results of each individual measuring point and thus the total result will be more precise, as inaccuracies of measuring points covered only partially are reduced or even avoided.

Further, due to the evaluation of the complex impedance and especially the real part thereof the respective surface can be concluded, if an average thickness is assumed for the particular volume.

In addition, the control and evaluating unit 22 may control the individual antennas 16 of the sensor 14 in a synchronized manner so that measurements of the biomolecules in the operators blood are carried out at regular intervals.

The values detected by the control and evaluating unit 22 may be stored in a memory 24, thus allowing the control and evaluating unit 22 to extrapolate courses by way of the stored values so as to predict a development.

In this way, the operator of a vehicle operating element 12 can be warned in good time in the case of continuous increase in a particular biomolecule, for example, if due to the extrapolation the corresponding concentration has to be expected to exceed a threshold stored in the memory 24.

For this purpose, the control and evaluating unit 22 is connected to a central control unit 26 of the vehicle which in turn is connected to at least one vehicle system 28. The control and evaluating unit 22 makes the evaluated data available to the central control unit 26 so that the latter controls and/or governs the vehicle instrument 28 on the basis of the established concentration values. The vehicle system 28 may be, for instance, a distance and/or speed control unit, air conditioning, display element, loudspeaker, lane-keeping system, traffic jam assistant and/or steering assistant.

Further, the central control unit 26 may take over all functions of the vehicle and initiate a brake action, wherein it can also make an emergency call. This extreme case is provided especially when a current measurement has resulted in an extremely critical concentration value of a biomolecule which in the normal case results in immediate unfitness to drive of the operator.

Figure 2:
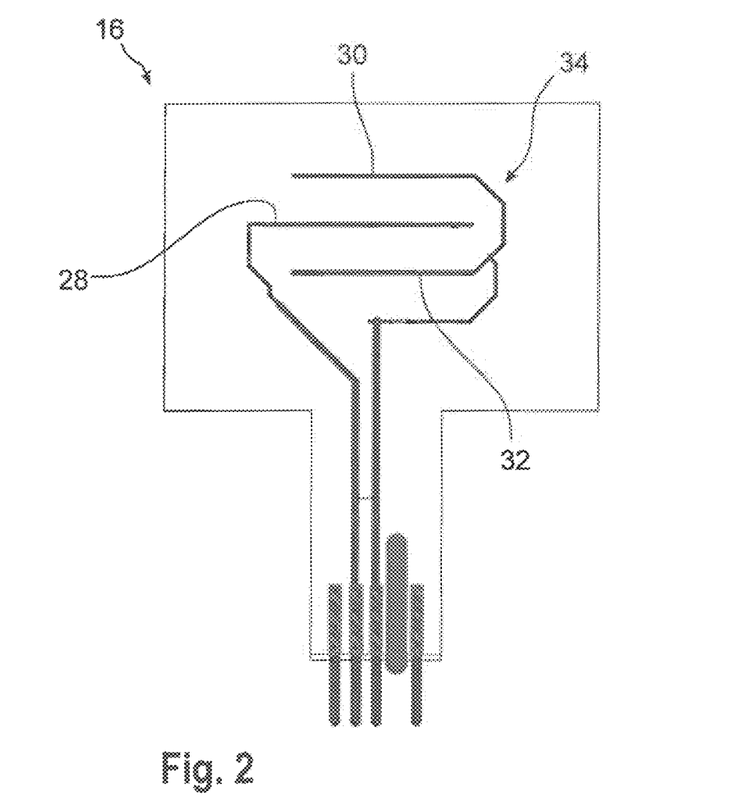
FIG. 2 shows a schematic representation of an antenna used in the invention according to a first embodiment.
Figure 7:
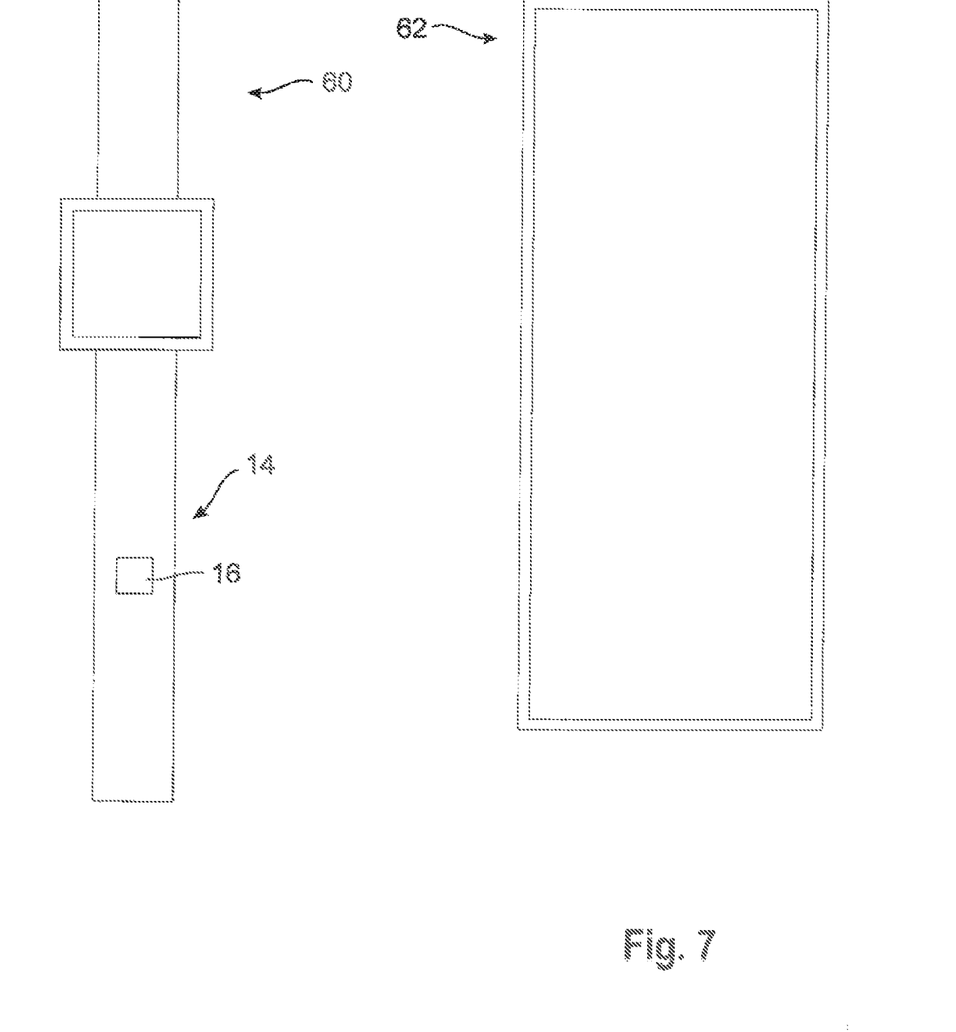
FIG. 7 shows a schematic representation of a measuring instrument according to the invention.

FIG. 2 schematically illustrates a first embodiment of an antenna 16, as it may be used in the vehicle operating element 12 or in a measuring instrument 60 (cf. FIG. 7).

In general, the antenna 16 is designed to be flexible so that it may be attached to the typically circular steering wheel rim in a simple manner by arranging it curved around the steering wheel rim.

The antenna 16 includes a first conductor 28 connected to a first electrical potential, for instance ground.

Moreover, the antenna 16 has a second conductor 30 which is connected to a second electrical potential deviating from the first electrical potential. Current, especially alternating current, is supplied to the second conductor 30 for example by the control and evaluating unit 22 so that appropriate excitation signals for the biomolecules in the blood of the operator are emitted via the antenna 16.

In the shown embodiment, the antenna 16 includes a third conductor 32 which is electrically coupled to the second conductor 30 and together with the latter forms a connecting conductor 34.

The conductors 28 to 32 are aligned in parallel, with the second conductor 30 and the third conductor 32 being spaced apart from each other so that the first conductor 28 is sandwiched centrally therebetween.

In general, the connecting conductor 34 in the shown section is "C-shaped" so that the first conductor 28 protrudes from the open side of the "C" into the connecting conductor 34 and is provided centrally between the two spaced conductors 30, 32 of the connecting conductor 34. In this way, both between the first conductor 28 and the second conductor 30 and between the first conductor 28 and the third conductor 32 an electric field that serves for generating the excitation signals may form. Therefore, the efficiency of an antenna 16 of such structure is especially high.

Figure 3:
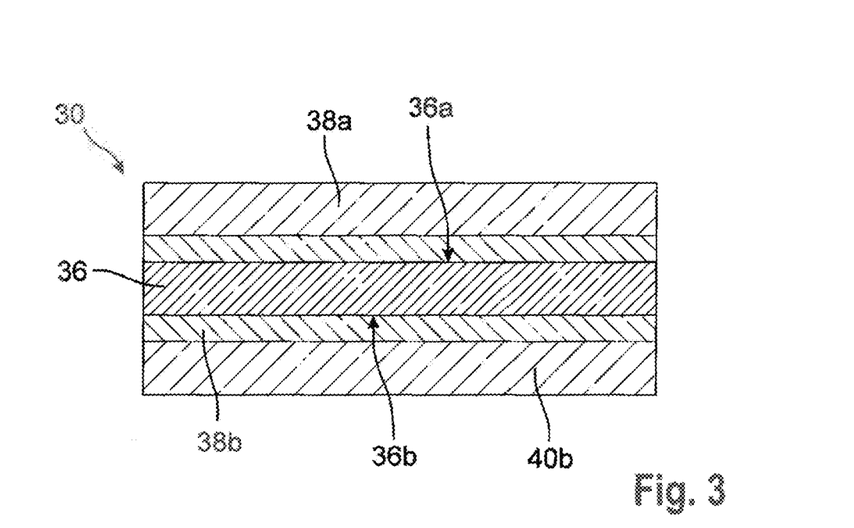
FIG. 3 shows a schematic representation of the layered structure of a conductor of an antenna used in the invention.

One cannot take from FIG. 2 that the individual conductors 28 to 32 are separated from each other by an insulating layer. This is shown in FIG. 3, however, in which the structure of a conductor is exemplified by way of the second electrical conductor 24. In general, the other electrical conductors 28, 32 are designed analogously.

FIG. 3 illustrates that the second conductor 30 includes a centrally arranged second conductive layer 36 which is made from copper, for example. Opposed sides 36a, 36b of the conductive layer 36 are provided with an upper bond layer 38a and a lower bond layer 38b. The bond layer 38a, 38b may be an epoxy resin, for example.

Via the upper bond layer 38a an upper insulating layer 40a is connected to the upper side 36a of the conductive layer 36 of the second conductor 30. Accordingly, a lower insulating layer 40b is connected to the lower side 36b of the conductive layer 36. The insulating layers 40a, 40b may be made from polyimide, especially in the form of a Kapton film.

In general, the conductive layer 36 is surrounded from both sides 36a, 36b by an electrically insulating layer 40a, 40b so that the second conductive layer 36 and the second conductor 30 are electrically insulated.

The second conductor 30 may especially be a thin-walled and flexible conductor path in which the conductive layer 36 has been laminated or vapor-deposited to the lower insulating layer 40b.

Figure 4:
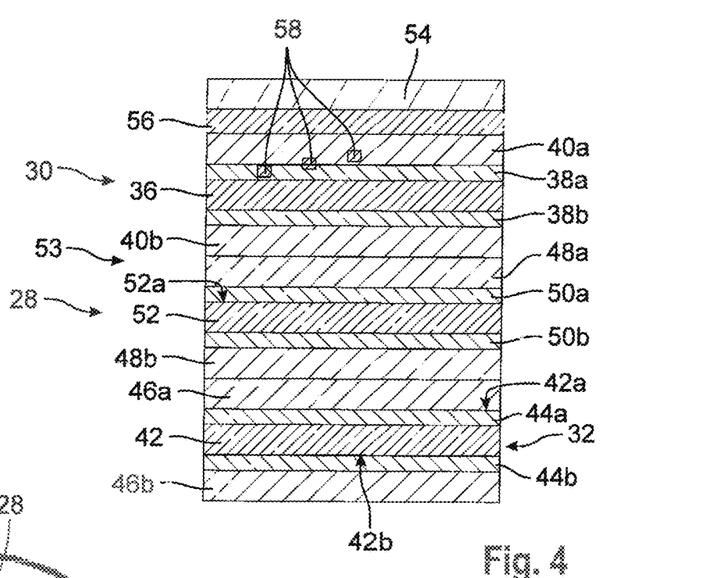
FIG. 4 is a schematic sectional view of the antenna from FIG. 2.

In FIG. 4 a section across the conductor structure of the antenna 16 of FIG. 2 is schematically illustrated, wherefrom it is evident that all conductors 28 to 32 are designed analogously to the second conductor 30 of FIG. 3.

Accordingly, the third conductor 32 equally comprises a centrally arranged third conductive layer 42 which is connected to a respective insulating layer 46a, 46b by means of two respective bond layers 44a, 44b so that the third electrically conductive layer 42 is equally electrically insulated from both sides 42a, 42b.

Adjacent to the upper insulating layer 46a of the third conductor 32 is a lower insulating layer 48b of the first conductor 28 which is equally connected to a first conductive layer 52 via a lower bond layer 50b.

Toward the upper side 52a the first electrically conductive layer 52 is connected via an upper bond layer 50a to an upper insulating layer 48a which is directly adjacent to the lower insulating layer 40b of the second conductive layer 36.

Since the second conductor 30 and the third conductor 32 jointly form the connecting conductor 34, the second conductive layer 36 and the third conductive layer 42 form an appropriate connecting layer 53 having a C-shaped section so that the first conductive layer 52 protrudes into the C-shaped connecting layer 53. In this way, generally a fork-type structure of the conductors 28 to 32 as well as of the electrically conductive layers 36, 42, 52 is formed.

When each of the conductors 23 to 32 is designed of separately manufactured conductive paths which are jointly formed to constitute the antenna 16, each of the conductors 28 to 32 includes such layered structure.

Alternatively, it may also be provided, however, that neighboring insulating layers are integrally formed, unless the antenna 16 is not formed of different conductors.

From FIG. 4 it is further evident that an optional cover layer 54 resting on the second layer 30 may be provided. The cover layer 54 is contacted by the operator of the vehicle operating element 12 during operation of the vehicle operating element 10 and therefore is made from a haptically and visually appealing material. The sensor 14 is not visible to the operator of the vehicle.

The cover layer 54 is made from electrically insulating material so that the function of the antenna 16 is not disturbed. Said material may especially be a film, diaphragm, leather skin, wooden layer, ceramics, glass or varnish, wherein the materiel is dependent on the environment into which the antenna 16 is to be introduced.

It can further be seen from FIG. 4 that an optional heating layer 56 may be provided which is arranged in the area of an insulating layer, in this case of the upper insulating layer 40a of the first conductive layer 36.

The heating layer 56 may be a copper layer (or copper wires) being consequently configured analogously to any one of the electrically conductive layers 36, 42, 52. The heating layer 56 helps to ensure that the vehicle operating element 12 may be heated, if needed, so as to increase the comfort for the operator of the vehicle operating element 12.

The heating layer 56 may also be coupled to the control and evaluating unit 22 to take over control of the heating layer 56.

As an alternative, any one of the electrically conductive layers 36, 42, 52 may be controlled by the control and evaluating unit 22 so that it heats and thus acts as an additional heating layer.

Moreover, it is evident from FIG. 4 that the antenna 16 may include dielectric inserts 58 being arranged in the illustrated embodiment as particles inside the layers of the antenna 16, especially in any one of the insulating layers or any one of the bond layers.

The dielectric inserts 56 may be ceramic or fine ceramic parts which serve for improving the sensitivity of the antenna 16 in the low frequency range, as the dielectric properties of the antenna 16 generally vary by a dielectric insert 58.

Alternatively, also a continuous layer made from fine ceramics may be provided.

Figure 5:
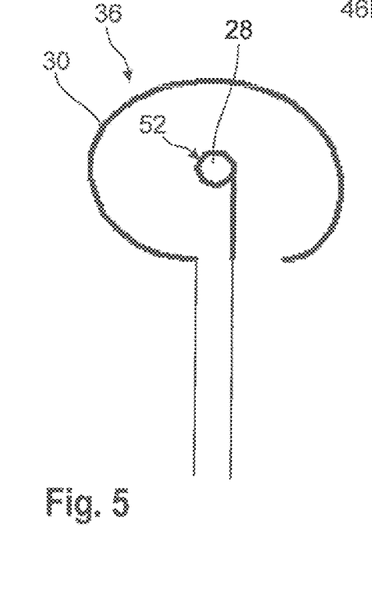
FIG. 5 shows a schematic representation of an antenna used in the invention according to a second embodiment.

FIG. 5 shows a second embodiment of the antenna 16 comprising two conductors 28, 30 and thus only two conductive layers 36, 52, the second conductor 30 and, consequently, the second conductive layer 36 being curved and extending around the circular first conductor 30 and the equally circular-shaped first conductive layer 52.

The two conductors 28, 30 are arranged eccentrically relative to each other so as to be capable of generating an appropriate excitation signal and of receiving an off-resonance excitation signal.

The second conductive layer 36 may include an edge-side structuring, thus causing the second conductive layer 36 to have a polygonal edge which allows the antenna 16 to exhibit larger frequency coverage due to the circular design of the first conductive layer 36 on the basis of the Sierpinski effect.

The embodiment of the antenna 16 shown in FIG. 5 excels by the fact that one pole of the antenna 16, i.e. the first conductive layer 52, has a round design, whereas the second pole of the antenna 16, i.e. the second electrically conductive layer 36, is polygonal. In this way, it is generally possible to detect large wavelengths lying within the range of meters by an antenna structure which is merely within the range of millimeters.

Figure 6:
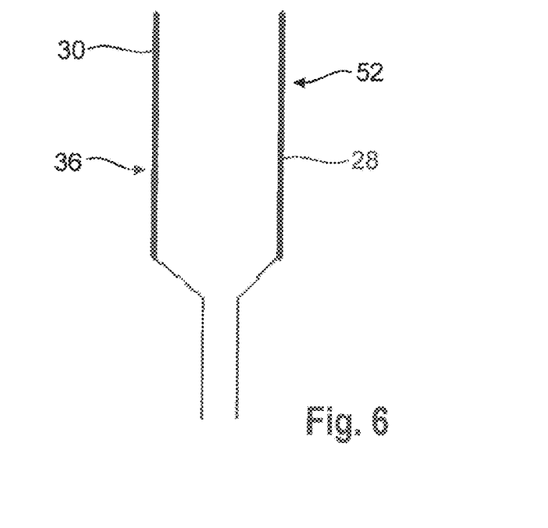
FIG. 6 shows a schematic representation of an antenna used in the invention according to a third embodiment.

From FIG. 6 a third embodiment of the antenna 16 is resulting which may be used in a vehicle operating element 12.

The third embodiment of the antenna 18 also includes merely two conductors 28, 30 which are parallel to each other. Hence also the two conductive layers 36, 52 are formed to be parallel to each other.

In general, due to the appropriate configuration of the conductive layers 36, 52 and the antenna 16, different excitation signals can be generated, thus enabling improved measurement of the biomolecules in the operator's blood in the case of specific arrangements of the sensor 14 and, resp., the antennas 16 on the vehicle operating element 12.

As an alternative to the shown steering wheel 10, a vehicle operating element may also be part of an actuating lever or shift lever so that the latter include the sensor 14. In this way, the sensor 14 may be disposed inside a door handle, an operating unit (switch) for vehicle electronics or any further components of the vehicle which are usually contacted by an operator.

FIG. 7 illustrates a measuring instrument 60 which in the shown embodiment is a wristwatch, especially a so-called smartwatch. The measuring instrument 60 includes at least one antenna 16 which is part of a sensor 14 by which biomolecules in the blood of an operator can be measured non-invasively.

In the shown embodiment the sensor 14 and, resp., the antenna 16 is/are provided in the wristband of the wristwatch. Alternatively, the antenna 16 may as well be provided on the rear side of the housing which contacts the operator's body.

The data detected by the sensor 14 are evaluated in the measuring instrument 60 itself or are wirelessly transmitted to the control and evaluating unit 22 of the vehicle for evaluation of the detected data.

Alternatively, the data may be transmitted from the measuring instrument 60 to an external evaluating unit 62 in the form of a cell phone, especially a smartphone, in the illustrated embodiment.

The cell phone may be coupled to the control and evaluating unit 22 of the vehicle so that the data are indirectly transmitted from the measuring instrument 60 to the control and evaluating unit 22 of the vehicle.

Instead of the wristwatch, the measuring instrument 60 may as well be a fitness wristband or any other accessory which the operator is wearing and which does not disturb him/her in operating the vehicle.

The invention claimed is:

1. A vehicle operating element (12) comprising at least one sensor (14) for non-invasive measurement of biomolecules in the blood of an operator of the vehicle operating element (12) by means of electrochemical impedance spectroscopy, comprising at least one antenna (16) which includes at least a first conductive layer (52), a second conductive layer (36), an insulating layer (40b, 48a) being sandwiched between the second and first conductive layers (36, 52), and a third conductive layer (42) electrically coupled to the first or second conductive layer (52, 36) and forming a connecting layer (53) with the electrically coupled first or second conductive layer (52, 36), wherein the conductive layers of the connecting layer (53) are spaced apart from each other and the second or first conductive layer (36, 52) is sandwiched between the conductive layers of the connecting layer (53), and wherein by means of the first conductive layer (52) and/or the second conductive layer (36) an excitation signal is coupled out and an off-resonance excitation signal is coupled into the antenna (16).

2. The vehicle operating element (12) according to claim 1, wherein the first or second conductive layer (36, 52) is configured to have an edge-side structuring to exhibit a polygonal edge.

3. The vehicle operating element (12) according to claim 1, wherein the first conductive layer (52) and the second conductive layer (36) are arranged in parallel to each other.

4. The vehicle operating element (12) according to claim 1, wherein the electrically conductive layers (36, 42, 52) are flexible.

5. The vehicle operating element (12) according to claim 1, wherein a cover layer (54) to be contacted by the operator is provided which is the outermost layer of the antenna (16) and is made from an electrically insulating material.

6. The vehicle operating element (12) according claim 1, wherein the antenna (16) is a dipolar antenna or a multipolar antenna.

7. The vehicle operating element (12) according to claim 1, wherein the antenna (16) comprises a dielectric insert (58) for improving the sensitivity of the antenna (16) in the low frequency range.

8. The vehicle operating element (12) according to claim 1, wherein a control and evaluating unit (22) for controlling the at least one antenna (16) and for evaluating the off-resonance excitation signals received by the at least one antenna (16) is provided.

9. The vehicle operating element (12) according to claim 8, wherein the control and evaluating unit (22) is configured to generate different excitation frequencies for the antenna (16).

10. The vehicle operating element (12) according to claim 8, wherein the control and evaluating unit (22) is configured to evaluate wave functions of off-resonance excitation signals and, on the basis of the off-resonance, establish the presence of biomolecules.

11. The vehicle operating element (12) according to claim 1, wherein the vehicle operating element (12) is part of a vehicle steering wheel (10), actuating lever or shift lever of the vehicle.

12. The vehicle operating element (12) according to claim 1, wherein plural antennas (16) are arranged and spread over the vehicle operating element (12).

13. The vehicle operating element (12) according to claim 1, wherein there is provided a heating layer (56) which is adjacent to or integrated in an insulating layer (40a, 40b, 46a, 46b, 48a, 48b).

14. A method of non-invasive measurement of biomolecules in the blood of an operator of a vehicle by means of electrochemical impedance spectroscopy using a vehicle operating element (12) according to claim 1.

15. The method according to claim 14, wherein plural biomolecules having different excitation frequencies are measured.

16. The method according to claim 14, wherein the measurement of the biomolecules in the operator's blood is carried out contact-less.

17. The method according to claim 14, wherein a control and evaluating unit (22) evaluates the complex impedance between the excitation signal and the off-resonance excitation signal for quantifying the concentration of the biomolecules in the operator's blood.

18. The method according to claim 17, wherein the real part of the complex impedance for determining the sample volume and the imaginary part of the complex impedance is evaluated for quantifying the biomolecules to calculate the concentration of the biomolecules.

19. The method according to claim 17, wherein, on the basis of the complex impedance, the control and evaluating unit (22) determines the measuring surface and/or the measuring points and/or the number of operators underlying the measurement.

20. The method according to claim 14, wherein a control and evaluating unit (22) controls the at least one antenna (16) in a synchronized manner, wherein, if plural antennas (16) are provided, the control and evaluating unit (22) sequentially controls the antennas (16).

21. The method according to claim 14, wherein a memory (24) is provided in which the established values can be stored, wherein a control and evaluating unit (22) calculates trends for establishing forecasts about the development of the values on the basis of the stored values.

22. A measuring instrument for non-invasive measurement of biomolecules in the blood of an operator of a vehicle by means of electrochemical impedance spectroscopy, comprising at least one antenna (16) which includes at least a first conductive layer (52), a second conductive layer (36), and a third conductive layer (42) electrically coupled to the first or second conductive layer (36, 52) and forming a connecting layer (53) with the electrically coupled first or second conductive layer (52, 36), wherein the conductive layers of the connecting layer (53) are spaced apart from each other and the second or first conductive layer (36, 52) is sandwiched between the conductive layers of the connecting layer (53), and wherein the measuring instrument is coupled to a control and evaluating unit (22) of the vehicle.

23. The measuring instrument according to claim 22, wherein the at least one antenna (16) further comprises an insulating layer (40b, 48a) sandwiched between the two conductive layers (36, 52), and wherein by means of the first conductive layer (52) and/or the second conductive layer (36) an excitation signal is coupled out and an off-resonance excitation signal is coupled into the antenna (16).

24. A method of non-invasive measurement of biomolecules in the blood of an operator of a vehicle by means of electrochemical impedance spectroscopy using a measuring instrument according to claim 22.

25. A method of operating a vehicle, wherein a method of non-invasive measurement of biomolecules according to claim 14 is carried out, wherein at least one vehicle system (28) is operated depending on the result of the method of non-invasive measurement of biomolecules.

26. A method of operating a vehicle, wherein a method of non-invasive measurement of biomolecules according to claim 24 is carried out, wherein at least one vehicle system (28) is operated depending on the result of the method of non-invasive measurement of biomolecules.

27. The vehicle operating element (12) according to claim 7, wherein the dielectric insert (58) is made from fine ceramics.

28. The method according to claim 14, wherein the biomolecules to be measured are lactate, alcohol, and/or urea.

29. The measuring instrument according to claim 22, wherein the biomolecules to be measured are lactate, alcohol, and/or urea.

30. The method according to claim 24, wherein the biomolecules to be measured are lactate, alcohol, and/or urea.

* * * * *